United States Patent [19]

Sweeney et al.

[11] Patent Number: 5,026,355

[45] Date of Patent: Jun. 25, 1991

[54] NEEDLE AND HUB ASSEMBLY WITH NEEDLE CONTACTING MEMBER

[75] Inventors: Niall Sweeney, East Rutherford; Sandor Gyure, West Orange, both of N.J.

[73] Assignee: Becton Dickinson and Company, Franklin Lakes, N.J.

[21] Appl. No.: 468,495

[22] Filed: Jan. 23, 1990

[51] Int. Cl.$^5$ ............................................... A61M 5/31
[52] U.S. Cl. ..................................... 604/243; 604/240
[58] Field of Search ................................. 604/240–243, 604/272, 273, 263

[56] References Cited

U.S. PATENT DOCUMENTS

| | | | |
|---|---|---|---|
| 1,705,525 | 3/1929 | Hofschneider | 604/243 |
| 2,806,473 | 9/1957 | Lingley | 604/243 |
| 3,035,616 | 5/1962 | Hamilton | 604/243 X |
| 3,186,408 | 6/1965 | Jacob . | |
| 3,372,697 | 3/1968 | Keller | 604/241 |
| 3,430,627 | 3/1969 | Kitaj . | |
| 3,472,227 | 10/1969 | Burke . | |
| 3,523,532 | 8/1970 | Burke . | |
| 3,523,533 | 8/1970 | Burke . | |
| 3,550,581 | 12/1970 | Boyle | 604/272 X |
| 4,040,421 | 8/1977 | Young | 604/243 X |
| 4,240,425 | 12/1980 | Atchavi | 604/243 X |
| 4,581,024 | 4/1986 | Swenson . | |
| 4,795,445 | 1/1989 | Jensen | 604/240 |

Primary Examiner—John D. Yasko
Assistant Examiner—Adam J. Cermak
Attorney, Agent, or Firm—John L. Voellmicke

[57] ABSTRACT

A needle assembly includes an elongate cannula having a first end, an opposite end and a sidewall therebetween. The cannula includes a lumen therethrough defining a cannula longitudinal axis. A hub having a proximal end, a distal end and a passageway therethrough defining a longitudinal axis is provided. The passageway includes an enlarged first portion at the distal end, a second portion adjacent to the first portion and a third portion adjacent to the proximal end. The cannula is positioned in the hub so that the opposite end is within the second portion and the first end projects outwardly from the distal end of the hub. The second portion includes a proximally located ledge for establishing the most proximal position of the cannula in the passageway and an inwardly projecting flange, located distally from the ledge, for contacting and holding a cannula with sufficient force to prevent the cannula from falling out of the hub. The annular flange and the ledge interact with the cannula so that the angular relationship between the cannula longitudinal axis and the hub longitudinal axis can be varied and the cannula movably held in a selected angular relationship. Adhesive is provided in the volume described by the first portion for holding the cannula fixedly in the selected angular relationship with respect to the hub.

18 Claims, 5 Drawing Sheets

NEEDLE AND HUB ASSEMBLY WITH NEEDLE CONTACTING MEMBER

BACKGROUND OF THE INVENTION

1. Field of the Invention

The present invention relates to a needle assembly and more particularly concerns an improved needle assembly for use with or as part of a hypodermic syringe or other fluid transferring device.

2. Description of Related Information

Hypodermic needle assemblies, including a cannula and a hub, are oftentimes removably attached to syringes for performing a variety of tasks such as the administration of medication to patients and into devices and for the withdrawing of fluid samples from patients and from fluid sources. In some cases the cannula is attached directly to the syringe barrel, thus eliminating the hub. Further, many fluid delivery tube sets, fittings and stopcocks have a standard luer or locking luer fitting so that needle assemblies may be used in a variety of drug delivery systems such as in intravenous (IV) therapy and in a variety of fluid handling laboratory setups. Needle assemblies are also used for blood collection and in industrial applications such as dispensing liquids.

A fundamental requirement for a cannula and hub assembly, and an assembly of a cannula and a syringe barrel, is that the resulting assembly be capable of holding the cannula so that it is firmly connected to the hub or syringe and cannot be easily removed therefrom. Also, the cannula should be substantially aligned with the longitudinal axis of the hub or syringe barrel and not projecting angularly therefrom. An important negative consequence of a misaligned cannula occurs in the manufacturing process because the sharp cannula tip can be extensively damaged by engaging the inside wall of the rigid needle shield when the needle shield is placed over the cannula to engage the hub. Proper alignment between the cannula and the hub and/or syringe barrel is important to help the user properly guide the cannula into the patient's body during injection when reshielding the cannula. Further, the manufacturing process used should not create particles or debris in the lumen of the cannula which may later be injected into the patient presenting a potential health hazard.

From a manufacturing process point of view, it can be undesirable to provide a hub which has a cannula receiving bore which is smaller than the outside diameter of the cannula. It is believed that, unless dimensional tolerances are carefully controlled, forcing the hollow cannula through a smaller bore, especially with a plastic hub, allows the fine edges of the cannula to potentially skive plastic material from the hub inside diameter wherein this material may be later injected into the patient. Also, the forced assembly of a cannula and hub presents quality problems during mass production because of the difficulty in controlling the forces involved. The forces required for cannula insertion may be large enough to bend or buckle the cannula, or drive the cannula too far into the hub or through the hub. This is especially true when many cannula hub assemblies are being processed at the same time. Finally, placing a cannula in a long cannula receiving bore may result in the cannula being at an angular orientation with respect to the hub and/or barrel. This angular orientation is the result of molding tolerances and cannot be adjusted if a more optimal angular relationship is required.

Cannula and hub assemblies wherein adhesive is used to bond the cannula to the hub may also present problems where the hub structure allows the adhesive to nearly contact the open proximal end of the cannula because if the adhesive flows into the cannula lumen there is a potential for clogging the cannula. Also, attempting to apply adhesive deeply into the space between hub and loosely fitting cannula presents quality control problems because the process becomes sensitive to the viscosity, temperature and delivery pressure of the adhesive.

U.S. Pat. No. 3,186,408 to Jacob teaches a cannula and hub assembly wherein the cannula mounting portion of the hub has a greater inside diameter than the outside diameter of the cannula so that the space therebetween can be filled with adhesive. Jacob does not appear to provide structure to assure the alignment of the cannula with the hub. The Jacob design, theoretically, allows the adhesive to cover all of that portion of the cannula which is within the hub and potentially to enter the lumen of the cannula.

U.S. Pat. No. 3,472,227 to Burke teaches an improved cannula hub assembly wherein the proximal end of the cannula is physically engaged in the hub, in an interference or frictional fit, to maintain the relative position between the cannula and the hub. This interference would appear to prevent adhesive from passing through to the proximal end of the cannula. Although Burke provides structure to prevent the undesirable entry of adhesive into the cannula, the structure of Burke neither eliminates the potential for skiving hub material into the cannula lumen nor provides a positive stop to position the cannula within the hub. Burke also appears to provide a structure which will not allow for the angular alignment of the needle after it is positioned within the hub.

Burke, in U.S. Pat. No. 3,523,533, teaches a three piece needle hub assembly which has a snap in limit stop provided to contact the proximal end of the cannula while distally placed inwardly positioned ribs engage the cannula upon insertion. After assembly, adhesive is apparently injected between the ribs to fill the cavity in the hub. Here, Burke's design allows potential for skiving of hub material and provides potential for adhesive to enter the proximal end of the cannula. Further, the additional snap in limit stop adds to the complexity of the cannula hub assembly and increases the number of dimensional tolerances which can negatively affect the alignment of the cannula and the hub, without provision for changing the alignment of the cannula in the hub after assembly and before application of adhesive to the structure.

Burke, in U.S. Pat. No. 3,523,532 teaches another three-piece cannula nd hub assembly which is functionally similar to the above mentioned U.S. Pat. No. 3,523,533 to Burke, except that the third component is snapped in from the distal end of the hub rather than from the proximal end. Here again, there is the potential for skiving hub material into the lumen, and also potential for entry of the adhesive into the lumen of the cannula.

U.S. Pat. No. 3,430,627 to Kitaj illustrates a typical cannula syringe tip assembly wherein the syringe tip contains a bore which is larger than the outside diameter of the cannula providing a space for adhesive to be introduced. The structure illustrated in the Kitaj patent does not provide structure for the alignment of the cannula with the syringe barrel and does not appear to eliminate the possibility of adhesive entering the proximal end of the cannula.

U.S. Pat. No. 4,581,024 to Swenson teaches a needle assembly to eliminate potential problems regarding skiving by providing a hub with a passageway which is larger than the needle. Swenson's passageway is enlarged at the distal end of the needle hub so that the adhesive used to assemble the needle to the hub is positioned at the end of the passageway opposite to the open proximal end of the cannula to minimize the possibility of adhesive entering the cannula lumen. Swenson's needle assembly, however, does not allow the controlled adjustment of the angular alignment between the needle cannula and hub.

The prior art teaches a wide variety of structures of cannula and hub assemblies. However, there is still a need for a simple, straight forward, reliable, easily fabricated needle assembly which provides needle hub structure which allows adjustment of the angular alignment between the needle cannula and the hub while providing structure which eliminates or minimizes the potential for adhesive entering the cannula lumen and structure which is less prone to skiving or scraping hub material during the assembly process.

SUMMARY OF THE INVENTION

The needle assembly of the present invention includes an elongate cannula having a first end, an opposite end and a sidewall therebetween. The cannula includes a lumen therethrough defining a cannula longitudinal axis. A hub includes a proximal end for engaging fluid transfer apparatus, a distal end and a passageway therethrough defining a hub longitudinal axis. The hub passageway includes an enlarged first portion at the distal end, a second portion adjacent to the first portion and a third portion adjacent to the proximal end. The first portion, second portion and third portion are in fluid communication. The cannula is positioned in the hub so that the opposite end is within the second portion and the first end of the cannula projects outwardly from the distal end of the hub. The second portion of the passageway includes a proximally located ledge for establishing the most proximal position of the cannula in the passageway. The second portion also includes inwardly projecting holding means, located distally from the ledge, for contacting and holding the cannula with sufficient force to prevent the cannula from falling out of the hub when the needle assembly is positioned in any static orientation while allowing the cannula to pivot with respect to the holding means. The holding means and the ledge interact with the cannula so that the angular relationship between the cannula longitudinal axis and the hub longitudinal axis can be varied and the cannula movably held in a selected angular relationship with respect to the hub. Adhesive is provided in the volume described by the first portion and the portion of the cannula sidewall within the first portion for holding the cannula fixedly and immovably in the selected angular relationship with respect to the hub.

Another embodiment of the instant invention includes a syringe assembly comprising a hollow barrel having a chamber for retaining fluid. A distal end of the barrel includes a barrel passageway therethrough communicating with the chamber. A stopper is slidably positioned in fluid tight engagement inside the barrel. The stopper is adapted to engage a plunger rod to facilitate its operation. The stopper is capable of moving fluid from the chamber through the passageway upon its movement toward the distal end and capable of facilitating the drawing of fluid into the chamber through the passageway upon its movement away from the distal end of the barrel. An elongate cannula having a first end, an opposite and a sidewall therebetween is provided. The cannula has a lumen therethrough defining a cannula longitudinal axis. Hub means at the distal end of the barrel includes a proximal end, a distal end and a passageway therethrough defining a hub longitudinal axis. The passageway includes an enlarged first portion at the distal end, a second portion adjacent to the first portion and a third portion adjacent to the proximal end and in fluid communication with the barrel passageway. The first portion, second portion and third portion are in fluid communication. The cannula is positioned in the hub means so that the opposite end is within the second portion and the first end projects outwardly from the distal end of the hub means. The second portion includes proximally located ledge for establishing the most proximal position of the cannula in the passageway. The second portion also includes inwardly projecting holding means, located distally from the ledge, for contacting and holding the cannula with sufficient force to prevent the cannula from falling out of the hub means when the syringe assembly is positioned in any static orientation while allowing the cannula to pivot with respect to the hub means. Adhesive is provided in the volume described by the first portion and the portion of the cannula sidewall within the first portion for holding the cannula fixedly and immovably in the selected angular relationship with respect to the hub means.

DETAILED DESCRIPTION

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-6, an improved needle assembly 20 includes an elongate cannula 21, a hub 22 and bonding material such as a quantity of adhesive 23 for joining the cannula and the hub. Needle assembly 20 may be used with a hypodermic syringe assembly 25 which typically includes a hollow barrel 27, a resilient stopper 28 and a plunger rod 29. Barrel 27 has an interior chamber 31 for retaining fluid. A tip 32 extends from the distal end of the barrel and contains a tip passageway 33 therethrough communicating with chamber 31.

For the purposes of the description of the present invention, the term "distal end" is meant to refer to the end furthest from the person holding the syringe, whereas the term "proximal end" is meant to refer to the end closest to the holder of the syringe.

Figure 1:
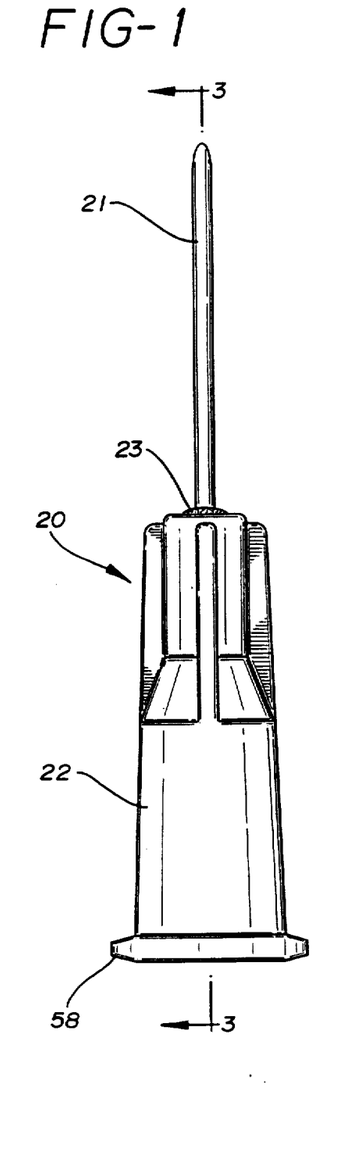
FIG. 1 is an enlarged side elevation view of the preferred needle assembly of the present invention.
Figure 2:
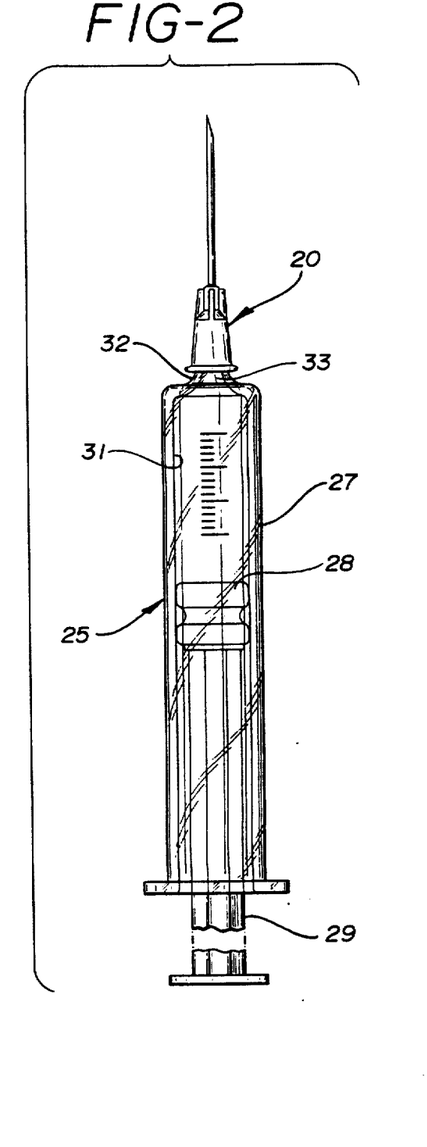
FIG. 2 is a side elevation view of the needle assembly of FIG. 1 attached to a hypodermic syringe.

Stopper 28 is slidably positioned in fluid tight engagement inside the barrel. Stopper 28 engages rigid plunger rod 29. In this embodiment, the stopper contains an internal thread (not shown) which engages an external thread (not shown) on the plunger rod. It will be apparent to one skilled in the art that numerous constructions can be used to join a stopper in a plunger rod and that the arrangement described herein is exemplary of these many possibilities. Also, it is within the purview of the instant invention to include a one piece plunger rod stopper assembly. The plunger rod is accessible outside of the proximal end of the barrel and is provided to move the stopper along the barrel to force fluid into or out of the chamber through tip passageway 33. Specifically, the stopper is capable of moving fluid from the chamber through the passageway upon its movement toward the distal end of the barrel, and the stopper is capable of facilitating the drawing of fluid into the chamber through the tip passageway upon its movement away from the distal end of the barrel.

Figure 3:
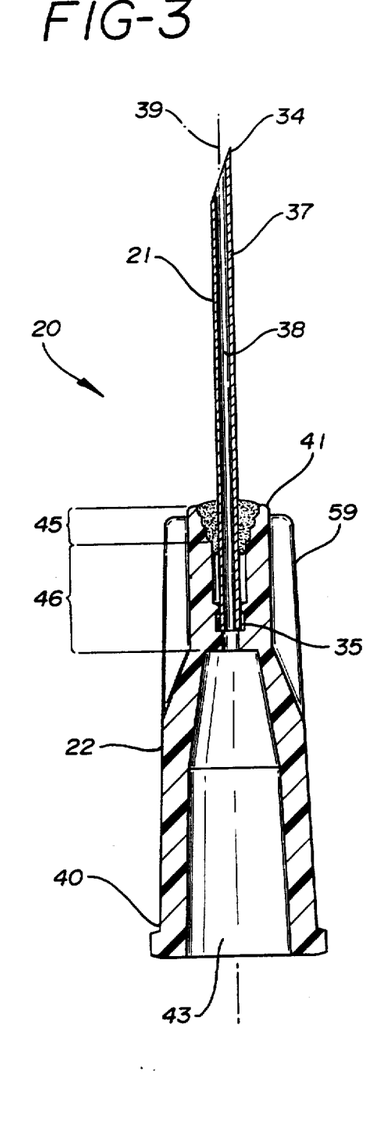
FIG. 3 is a cross sectional view of a needle assembly of FIG. 1 taken along line 3—3.

Elongate cannula 21 includes a first end 34, an opposite end 35 and a sidewall 37 therebetween. The cannula includes a lumen 38 defining a cannula longitudinal axis 39.

Figure 4:
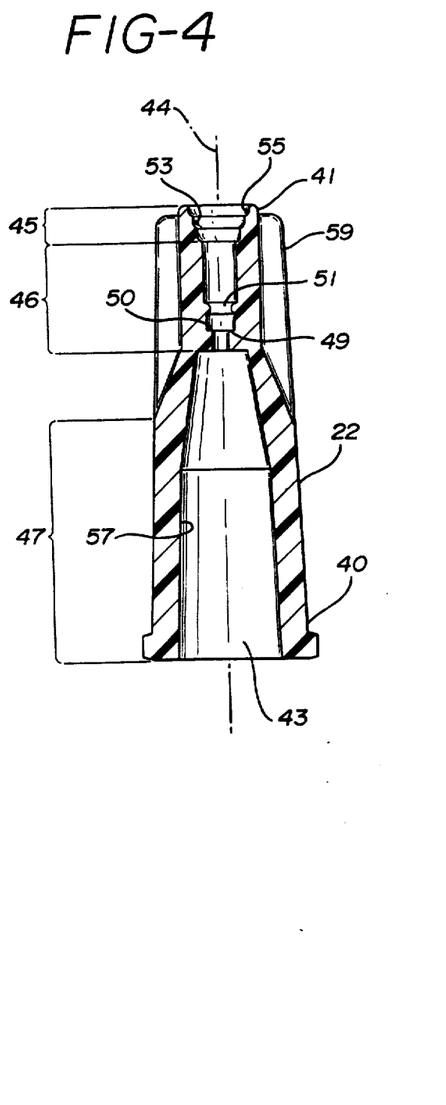
FIG. 4 is a cross sectional view of the hub of FIG. 3 shown without the cannula and the adhesive.

Hub 22 includes a proximal end 40 for engaging fluid transfer apparatus, a distal end 41 and a passageway 43 therethrough defining a hub longitudinal axis 44. Passageway 43 includes an enlarged first portion 45 at the distal end, a second portion 46 adjacent to the first portion and a third portion 47 adjacent to the proximal end of the hub. First portion 45, second portion 46 and third portion 47 are in fluid communication. The cannula is positioned in the hub so that opposite end 35 of the cannula is within second portion 46 and first end 34 of the cannula projects outwardly from the distal end of the hub.

Second portion 46 of the hub passageway includes a proximally located ledge means for establishing the most proximal position of the cannula in the passageway. In this embodiment, ledge means includes a ledge 49 having a cannula contacting surface 50 projecting inwardly in a plane substantially perpendicular to hub longitudinal axis 44. Although the ledge in this preferred embodiment is a continuous annular structure having a planar cannula contacting surface it is within the purview of the instant invention to include ledges of various structures including discontinuous and ledges having non-planar cannula contacting surfaces such as a frusto-conically shaped ledge which will be described hereinafter in an alternative embodiment. Contact between opposite end 35 of the cannula and cannula contacting surface 50 of ledge 49 limits the depth to which the cannula enters the hub and resists further proximally directed movement of the cannula with respect to the hub.

Second portion 46 also includes holding means, located distally from ledge 49, for contacting and holding the cannula with sufficient force to prevent the cannula from falling out of the hub when the needle assembly is positioned in any static orientation while allowing the cannula to pivot with respect to the holding means. In this preferred embodiment holding means includes an inwardly projecting annular collar 51 having an inside diameter which is slightly smaller than the outside diameter of cannula 21. The difference between the inside diameter described by the annular collar and the outside diameter of the cannula creates an interference fit between the cannula and the hub which is sufficient to hold the cannula from falling out of the hub even if it is oriented in an upside down position with the cannula facing downwardly. Holding means in the form of annular collar 51 and ledge means in the form of ledge 49 interact with the cannula so that the angular relationship between the cannula longitudinal axis and the hub longitudinal axis can be adjusted or varied and the cannula movably held in a selected angular relationship with the hub.

A quantity of adhesive 23 is placed preferably within the volume described by the enlarged first portion of the hub passageway and that portion of the cannula sidewall within first portion 45 of the passageway. The adhesive is provided for holding the cannula fixedly in a selected angular relationship with respect to the hub and for preventing the cannula from being pulled out of the hub during normal use. The first portion is enlarged to provide an adequate volume to hold adhesive. Alternating annular grooves 53 and ribs 55 provide structure for engaging the adhesive to further improve the joining of the adhesive to the first portion and to, increase the structural integrity of the needle assembly. As will be apparent to one skilled in the art, there are numerous structures that are known to improve the holding power between adhesive and a solid structure such as grooves, ribs, and modified surface finishes and that the alternating grooves and ribs shown herein are exemplary of these many possibilities.

Hub 22 preferably includes a tapered inside surface 57 which is sized and shaped to accept and removably engage tip 32 of hypodermic syringe 25 so that there is fluid communication between the interior chamber 31 of the syringe barrel through tip passageway 33 and hub passageway 43. Inside surface 57 may also accept and removably engage known I.V. tubing connectors and other known fluid flow fittings. External outwardly facing ribs 58 are provided to removably engage syringe tips or fluid flow fittings which contain a locking luer fitting (not shown). The hub also includes longitudinal external ribs 59 providing an engagement surface for a rigid cannula needle shield (not shown) which is removably positioned over the cannula to protect it before use and in some cases after use. It is an important feature of this invention that cannula alignment with respect to the hub may be controlled so that the cannula tip is less likely to be damaged when the rigid shield is installed on the hub.

A cannula and hub assembly of the preferred embodiment using a 22 gauge cannula, 0.028 inch (0.71 mm)

outside diameter preferably has a first portion having a maximum diameter, at the distal end of the hub, of approximately 0.075 inch (1.78 mm) and a length of approximately 0.090 inch (2.29 mm). The second portion is approximately inch 0.220 inch (5.59 mm) long with the inside diameter of the groove at annular collar 51 being approximately 0.027 inches (0.69 mm) inch.

Figure 5:
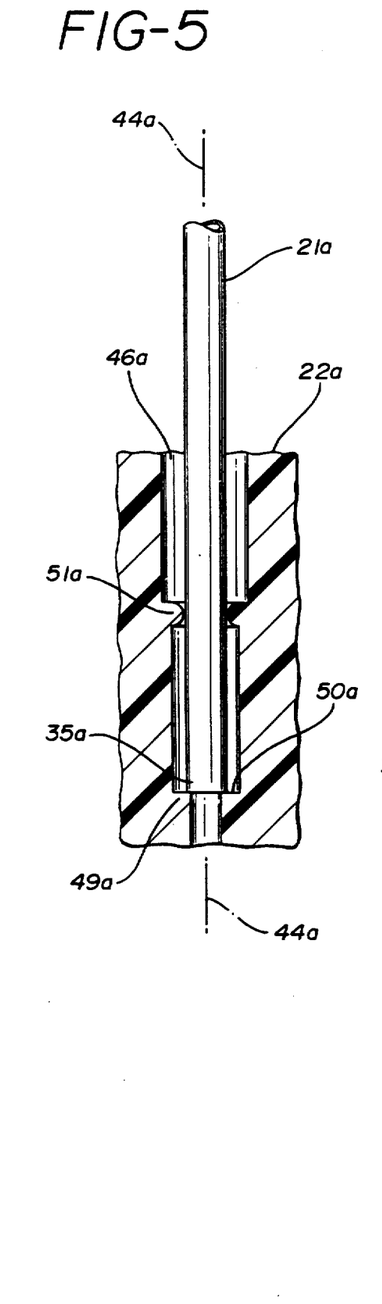
FIGS. 5 and 6 are a partial cross-sectional views illustrating portions of a hub and a cannula in accordance with the present invention to show how the structure of the hub can be used to provide various alignments of the cannula with respect to the hub.
Figure 6:
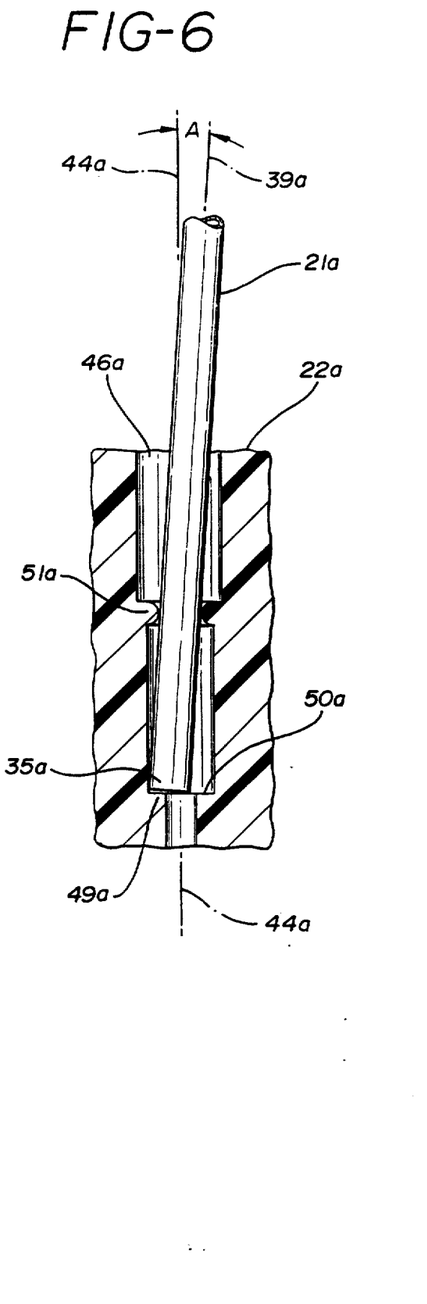

During assembly of the preferred needle assembly, the hub is oriented so that the distal end faces upwardly. A cannula is inserted, opposite end first, into the hub through the first portion and the second portion until the opposite end contacts cannula contacting surface of the ledge. As previously noted, cannula contacting surface 50 substantially limits how far the cannula enters the passageway. At this point the cannula alignment with respect to the hub may be satisfactory and within a pre determined specified range. However, if the alignment is not within specification the cannula may be moved angularly so that it pivots with respect to the annular collar while the opposite end of the cannula moves to a different position along the cannula contacting surface of the ledge. The interaction between the cannula and the hub can be better understood by referring to FIGS. 5 and 6. FIG. 5 illustrates a needle cannula 21a having a cannula longitudinal axis 39a in alignment with hub longitudinal axis 44a. FIG. 6 illustrates cannula 21a having its longitudinal axis 39a misaligned with hub longitudinal axis 44a at an angle of A. To change the orientation from that illustrated in FIG. 5 to that illustrated in FIG. 6 force is applied to the cannula to cause it to pivot around annular collar 51a so that opposite end 35a of the cannula moves to a different contacting position on cannula contacting surface 50a of ledge 49a in second portion 46a.

A key feature of the instant invention is that it allows adjusting the alignment of the needle cannula with respect to a hub and/or a syringe to compensate for manufacturing tolerances and uncontrollable variations in the product due to manufacturing variables. For example, if the hub means of the instant invention were integrally formed on a syringe barrel it may be that the orientation depicted in FIG. 6 would result in a perfect alignment of the syringe barrel with the needle cannula. That is, variations between the alignment of the hub passageway with respect to the syringe barrel may be compensated for by moving the needle within the structure taught by the instant invention.

It should be noted that the short distance of engagement between the cannula and the hub in the area of annular collar 51 substantially eliminates or reduces the potential for skiving or removing hub material while inserting the needle into the hub which is believed to exist in needle hub designs having long engagement conduits through which the cannula must be forced. Along with the potential for skiving, long engaging conduits eliminate the ability to adjust the angular relationship between the needle and the hub after initial assembly of the needle and the hub before adhesive is applied. Long engagement conduits increase the force required for cannula insertion. Such force may be large enough to bend or buckle the cannula or drive the cannula too far into the hub or through the hub.

It should be noted that the size of annular collar 51 is exaggerated for illustrating the features of the instant invention. A collar projecting inwardly in the passageway of the hub having a height of approximately 0.003 inches (0.076 mm) may be sufficient to achieve the desired result and still allow for the effective injection molding of the hub. Even with small annular collars the cannula alignment of the cannula longitudinal axis with respect to the hub longitudinal axis may be adjusted by about plus or minus two degrees which may be sufficient in many instances to achieve the desired result.

After the cannula longitudinal axis is properly aligned with the hub, adhesive may be applied to the needle assembly at enlarged first portion 45. Depending on the holding forces exerted on the cannula by the hub, and the viscosity of the adhesive and the manufacturing conditions, the cannula may or may not have to be held in alignment with the hub until the adhesive has set or cured. The concentration of the adhesive at the distal end of the hub, in the enlarged first portion, in the present invention allows the effective use of adhesives which must be exposed to specific conditions for curing, such as UV curable adhesive, because the adhesive is concentrated at a position where it may be readily exposed to the curing energy source. The hub of the present invention also facilitates the use of fast setting adhesives such as hot melt adhesives, which must fill the volume provided in a relatively short period of time, before setting. Also, the annular collar further functions to restrict the flow of adhesive toward the opposite end of the cannula by occluding a portion of the space within the second portion of the passageway outside of the cannula. Thus, it can be seen that the present invention provides structure for allowing the realignment between the cannula longitudinal axis and the hub longitudinal axis during assembly while reducing the generation of particles in the cannula lumen during assembly by providing minimum contact with the hub and reducing the potential for adhesive entering the lumen during assembly. This combination of improvements represents a substantial departure from the known prior art.

Figure 7:
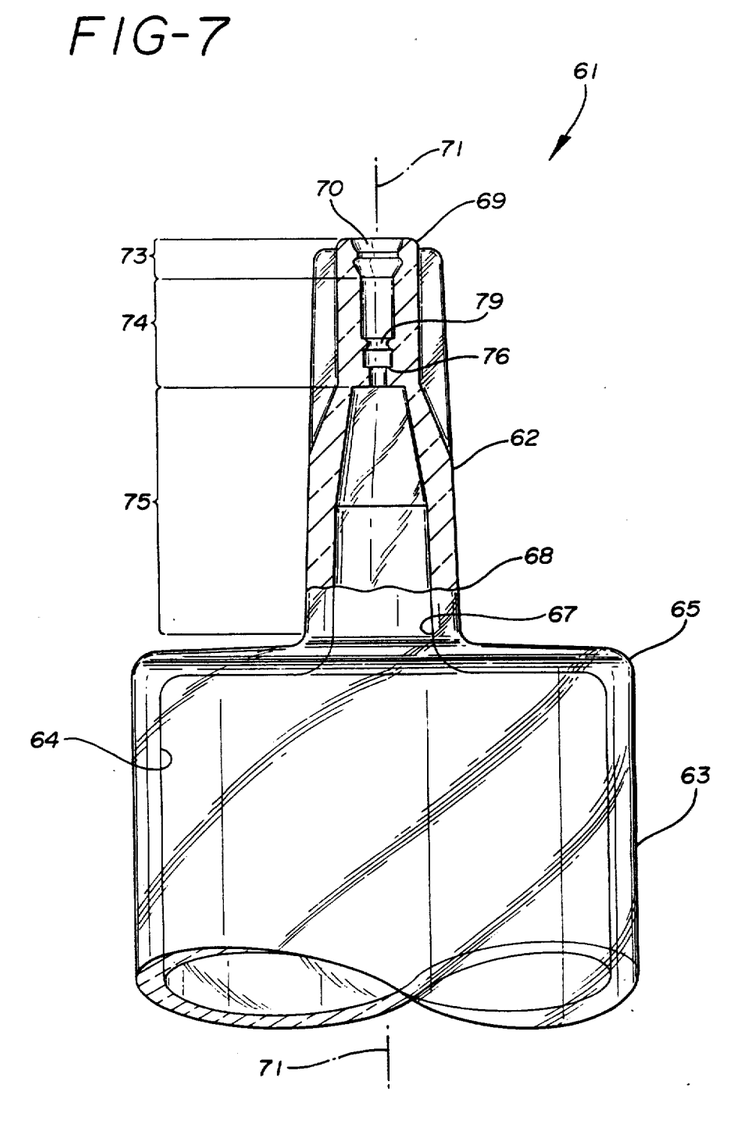
FIG. 7 is an enlarged partial cross-sectional view of an alternative embodiment of the present invention wherein the hub is integrally formed with a syringe barrel.

Referring now FIG. 7, an alternative embodiment 61 of the instant invention is substantially similar to the embodiment of FIGS. 1-4 with the exception that a hub 62 is integrally connected with a hollow syringe barrel 63. Barrel 63 includes chamber 64 for retaining fluid, a distal end 65 having a barrel passageway 67 therethrough communicating with the chamber. Hub 62 at the distal end of the barrel includes a proximal end 68, a distal end 69 and a passageway 70 therethrough defining longitudinal axis 71. Passageway 70 includes an enlarged first portion 73, a second portion 74 adjacent to the first portion, and a third portion 75 adjacent to the proximal end and in fluid communication with the barrel passageway. First portion 73, second portion 74, third portion 75 and barrel passageway 67 are in fluid communication. As in the embodiment of FIGS. 1-4, second portion 74 includes a proximally located ledge 76 projecting inwardly into the passageway for establishing the most proximal position of the cannula (not shown) in the passageway. The second portion also includes inwardly projected annular collar 79, located distally from ledge 76 for contacting and holding the cannula with sufficient force to prevent the cannula from falling out of the hub when the needle assembly of this embodiment is positioned in any static orientation while allowing the cannula to pivot with respect to the collar. The cannula (not shown) and bonding means (not shown) are substantially identical to those elements as taught hereinabove for the embodiment of FIGS. 1-4 and function in the same manner with the alternative embodiment of FIG. 7. The features of the instant invention are believed to be very desirable in this alternative embodiment because it is more difficult to achieve precise alignment of a hub passageway which is integrally molded over the long length of a syringe barrel. Accordingly, the instant invention provides structure for aligning the cannula with a long barrel and compensating for manufacturing variables and tolerances to achieve a hypodermic syringe assembly having an optimally aligned needle cannula.

Figure 8:
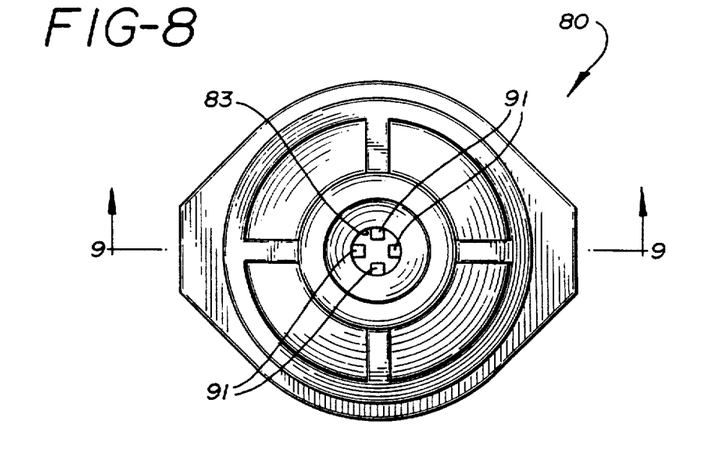
FIG. 8 is an enlarged top plan view of another alternative embodiment of the hub of the present invention showing cannula retention means in the form of four inward directly protuberances and a frusto conically shaped cannula contacting surface.
Figure 9:
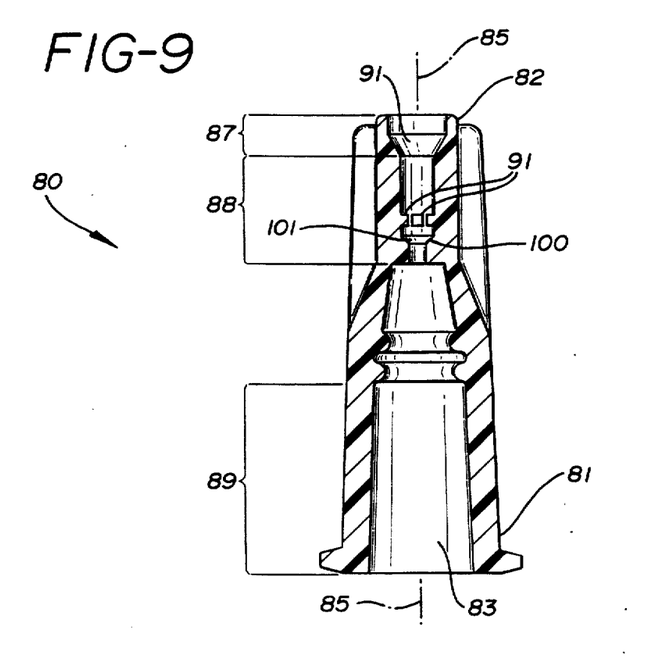
FIG. 9 is a cross sectional view of the hub of FIG. 8 taken along line 9—9.

Adverting to FIGS. 8 and 9 wherein an alternative hub 80 embodiment of the present invention is illustrated. Hub 80 includes a proximal end 81 for engaging fluid transfer apparatus, a distal end 82 and a passageway 83 therethrough defining a hub longitudinal axis 85. Passageway 83 includes an enlarged first portion 87 at the distal end, a second portion 88 adjacent to the first portion and a third portion 89 adjacent to the proximal end. First portion 87, second portion 88 and third portion 89 are in fluid communication.

The second portion includes proximally located ledge means for establishing the most proximal position of the cannula (not shown) in the passageway. In this embodiment the ledge means includes ledge 100 having a frusto conically shaped cannula contacting surface 101 tapered toward the proximal end of the hub. This embodiment includes holding means in the form of four inwardly directed protuberances 91 projecting into the passageway. Each protuberance having a free end 95. The free ends of each pair of opposed protuberances are separated by a distance which is smaller than the outside diameter of a cannula (not shown) to be used in a needle assembly with hub 80. Holding means in the form of protuberances are believed to be less tolerance dependent than the annular flange of FIGS. 1-4. Also, the protuberances in this embodiment allow air to freely escape from enlarged first portion 87 while adhesive is being added through the distal end of the passageway, thus minimizing the possibility of trapping an air bubble in a space provided for adhesive while still helping to obstruct the potential path of the adhesive through second portion 88 of the passageway.

In use, the needle assembly of the present invention may be attached to a hypodermic syringe which is then filled with liquid medication using known techniques. The syringe with needle assembly attached may then be used to inject the liquid medication into the patient's body, again, using known techniques. In the embodiment where the hub portion is integrally formed with the syringe barrel, the present invention may be used in the same manner described hereinabove except that it is not necessary to install the needle assembly onto the syringe barrel because the cannula is already attached to the syringe barrel.

The hub may be constructed of a wide variety of rigid material such as metals, plastics, ceramics and the like. Thermoplastic materials are preferred due to their low cost and proven compatibility with many liquid medications. A wide variety of materials including metals and plastics may be used to fabricate a cannula. However, in most cases a medical grade stainless steel is preferred. AA wide variety of adhesives such as hot metal adhesive, heat curable adhesive, UV curable adhesive and two part epoxy are suitable for bonding the cannula to the hub. It is preferred that all elements of the improved needle assembly be sterile when used. Accordingly, materials should be selected for compatibility with the sterilization process being used.

Thus, the present invention provides a simple, straight forward, reliable, easily fabricated improved needle assembly which provides needle hub structure which allows adjustment of the angular alignment between the needle cannula and the hub while providing structure which eliminates or minimizes the potential for adhesive entering the cannula lumen and provides structure which is less prone to skiving or scraping of hub material during assembly process and less likely to experience cannula point damage when a needle shield is attached.

What is claimed is:

1. A needle assembly comprising:

an elongate cannula having a first end, an opposite end and a sidewall therebetween, said cannula having a lumen therethrough defining a cannula longitudinal axis;

hub means having a proximal end for engaging fluid transfer apparatus, a distal end and a passageway therethrough defining a hub longitudinal axis;

said passageway having an enlarged first portion at said distal end, a second portion adjacent to said first portion and a third portion adjacent to said proximal end, said first portion, said second portion and said third portion being in fluid communication, said cannula being positioned in said hub means so that said opposite end is within said second portion and said first end projecting outwardly from said distal end of said hub means;

said second portion including proximally located ledge means for establishing the most proximal position of said cannula in said passageway, said second portion including inwardly projecting holding means, located distally from said ledge means, for contacting and holding said cannula with sufficient force to prevent said cannula from falling out of said hub means when said needle assembly is positioned in any static orientation while allowing said cannula to pivot with respect to said holding means, said holding means and said ledge means interacting with said cannula so that the angular relationship between said cannula longitudinal axis and said hub longitudinal axis can be varied and the cannula movably held in a selected angular relationship; and bonding means in the volume described by said first portion and the portion of said cannula sidewall within said first portion for holding said cannula fixedly in said selected angular relationship with respect to said hub.

2. The needle assembly of claim 1 wherein said holding means includes an inwardly projecting annular collar reducing said passageway to an inside diameter which is smaller than the outside diameter of said cannula.

3. The needle assembly of claim 2 wherein said collar is in a plane which is substantially perpendicular to said hub longitudinal axis.

4. The needle assembly of claim 1 wherein said holding means includes at least two inwardly directed protuberances projecting into said passageway, each protuberance having a free end, at least two of said free ends being separated by a distance smaller than the outside diameter of said cannula.

5. The needle assembly of claim 4 wherein said protuberances are spaced substantially equidistant with respect to each other around said hub longitudinal axis.

6. The needle assembly of claim 1 wherein said holding means is integrally formed with said hub means to form a one piece unitary structure.

7. The needle assembly of claim 1 wherein said ledge means includes a ledge having a cannula contacting surface projecting inwardly in a plane substantially perpendicular to said hub longitudinal axis.

8. The needle assembly of claim wherein said ledge means includes a frusto conically shaped cannula contacting surface tapering toward said proximal end of said hub means.

9. The needle assembly of claim 1 wherein said ledge means includes a plurality separate inclined cannula contacting surfaces positioned around the said hub longitudinal axis, each of said contacting surfaces inclined at substantially the same angle with respect to said hub longitudinal axis.

10. The needle assembly of claim 1 wherein said first end of said cannula has a sharpened edge.

11. The needle assembly of claim 1 wherein said first portion is substantially frustoconically shaped and is larger in diameter at said distal end than at the intersection of said first portion and said second portion of said passageway.

12. The needle assembly of claim 1 wherein said third portion of said passageway and said proximal end of said hub means are adapted to engage the tapered tip of a hypodermic syringe barrel so that said passageway is in fluid communication with the interior of the barrel.

13. The needle assembly of claim 1 wherein said proximal end of said hub means is integrally connected with an elongate syringe barrel having a hollow chamber for retaining fluids, a distal end of said barrel having a conduit therethrough communicating with said chamber, said conduit and said passageway being in fluid communication.

14. The needle assembly of claim 1 wherein said bonding means includes an adhesive selected from the group consisting of hot melt adhesive, heat curable adhesive, UV curable adhesive, and two part epoxy.

15. A needle assembly comprising:
an elongate cannula having a first end, an opposite end and a sidewall therebetween said cannula having a lumen therethrough defining a cannula longitudinal axis;
a hub having a proximal end for engaging fluid transfer apparatus, a distal end and a passageway therethrough defining a hub longitudinal axis;
said passageway having an enlarged first portion at said distal end, a second portion adjacent to said first portion and a third portion adjacent to said proximal end, said first portion, said second portion and said third portion being in fluid communication, said cannula being positioned in said hub means so that said opposite end is within said second portion and said first end projecting outwardly from said distal end of said hub means;
said second portion including proximally located ledge projecting inwardly into said passageway for establishing the most proximal position of said cannula in said passageway, said second portion including an inwardly projecting annular collar, located distally from said ledge for contacting and holding said cannula with sufficient force to prevent said cannula from falling out of said hub means when said needle assembly is positioned in any static orientation while allowing said cannula to pivot with respect to said collar;
said collar and said ledge interacting with said cannula so that the angular relationship between said cannula longitudinal axis and said hub longitudinal axis can be varied and the cannula movably held in a selected angular relationship; and
bonding means in the volume described by said first portion and the portion of said cannula sidewall within said first portion for holding said cannula fixedly in said selected angular relationship with respect to said hub.

16. The needle assembly of claim 15 wherein said third portion and said proximal end are adapted to engage the tapered tip of a hypodermic syringe barrel so that said passageway is in fluid communication with the interior of the barrel.

17. The needle assembly of claim 15 wherein said proximal end of said hub is integrally connected with an elongate syringe barrel having a hollow chamber for retaining fluids, a distal end of said barrel having a conduit therethrough communicating with said chamber, said conduit and said passageway being in fluid communication.

18. A syringe assembly comprising:
a hollow barrel having a chamber for retaining fluid, a distal end of said barrel having a barrel passageway therethrough communicating with said chamber;
a stopper slidably positioned in fluid-tight engagement inside said barrel adapted to engage a plunger rod to facilitate its operation, said stopper capable of moving fluid from said chamber through said passageway upon its movement toward said distal end, said stopper capable of facilitating the drawing of fluid into said chamber through said passageway upon its movement away from said distal end;
an elongate cannula having a first end, an opposite end and a sidewall therebetween, said cannula having a lumen therethrough defining a cannula longitudinal axis;
hub means at said distal end of said barrel having a proximal end, a distal end and a passageway therethrough defining a hub longitudinal axis;
said passageway having an enlarged first portion at said distal end, a second portion adjacent to said first portion and a third portion adjacent to said proximal end, and in fluid communication with said barrel passageway, said first portion, said second portion and said third portion being in fluid communication;
said cannula being positioned in said hub means so that said opposite end is within said second portion and said first end projecting outwardly from said distal end of said hub means;
said second portion including proximally located ledge means for establishing the most proximal position of said cannula in said passageway, said second portion including inwardly projecting holding means, located distally from said ledge means, for contacting and holding said cannula with sufficient force to prevent said cannula from falling out of said hub means when said syringe assembly is positioned in any static orientation while allowing said cannula to pivot with respect to said holding means, said holding means and said ledge means interacting with said cannula so that the angular relationship between said cannula longitudinal axis and said hub longitudinal axis can be varied and the cannula movably held in a selected angular relationship; and
bonding means in the volume described by said first portion and the portion of said cannula sidewall within said first portion for holding said cannula fixedly in said selected angular relationship with respect to said hub.

* * * * *

UNITED STATES PATENT AND TRADEMARK OFFICE
CERTIFICATE OF CORRECTION

PATENT NO. : 5,026,355

DATED : June 25, 1991

INVENTOR(S) : Niall Sweeney, et al

It is certified that error appears in the above-identified patent and that said Letters Patent is hereby corrected as shown below:

The title page should be deleted to appear as per attached title page.

The sheets of drawings consisting of Figs. 1 to 9 should be added as shown on the attached sheets.

Signed and Sealed this

Eighth Day of December, 1992

Attest:

DOUGLAS B. COMER

Attesting Officer

Acting Commissioner of Patents and Trademarks

United States Patent [19]

Sweeney et al.

[11] Patent Number: 5,026,355
[45] Date of Patent: Jun. 25, 1991

[54] NEEDLE AND HUB ASSEMBLY WITH NEEDLE CONTACTING MEMBER

[75] Inventors: Niall Sweeney, East Rutherford; Sandor Gyure, West Orange, both of N.J.

[73] Assignee: Becton Dickinson and Company, Franklin Lakes, N.J.

[21] Appl. No.: 468,495

[22] Filed: Jan. 23, 1990

[51] Int. Cl.⁵ .......................................... A61M 5/31
[52] U.S. Cl. .................................. 604/243; 604/240
[58] Field of Search ............................ 604/240-243, 604/272, 273, 263

[56] References Cited

U.S. PATENT DOCUMENTS

| | | | |
|---|---|---|---|
| 1,705,525 | 3/1929 | Hofschneider | 604/243 |
| 2,806,473 | 9/1957 | Lingley | 604/243 |
| 3,035,616 | 5/1962 | Hamilton | 604/243 X |
| 3,186,408 | 6/1965 | Jacob | |
| 3,372,697 | 3/1968 | Keller | 604/241 |
| 3,430,627 | 3/1969 | Kitaj | |
| 3,472,227 | 10/1969 | Burke | |
| 3,523,532 | 8/1970 | Burke | |
| 3,523,533 | 8/1970 | Burke | |
| 3,550,581 | 12/1970 | Boyle | 604/272 X |
| 4,040,421 | 8/1977 | Young | 604/243 X |
| 4,240,425 | 12/1980 | Atchavi | 604/243 X |
| 4,581,024 | 4/1986 | Swenson | |
| 4,795,445 | 1/1989 | Jensen | 604/240 |

Primary Examiner—John D. Yasko
Assistant Examiner—Adam J. Cermak
Attorney, Agent, or Firm—John L. Voellmicke

[57] ABSTRACT

A needle assembly includes an elongate cannula having a first end, an opposite end and a sidewall therebetween. The cannula includes a lumen therethrough defining a cannula longitudinal axis. A hub having a proximal end, a distal end and a passageway therethrough defining a longitudinal axis is provided. The passageway includes an enlarged first portion at the distal end, a second portion adjacent to the first portion and a third portion adjacent to the proximal end. The cannula is positioned in the hub so that the opposite end is within the second portion and the first end projects outwardly from the distal end of the hub. The second portion includes a proximally located ledge for establishing the most proximal position of the cannula in the passageway and an inwardly projecting flange, located distally from the ledge, for contacting and holding a cannula with sufficient force to prevent the cannula from falling out of the hub. The annular flange and the ledge interact with the cannula so that the angular relationship between the cannula longitudinal axis and the hub longitudinal axis can be varied and the cannula movably held in a selected angular relationship. Adhesive is provided in the volume described by the first portion for holding the cannula fixedly in the selected angular relationship with respect to the hub.

18 Claims, 5 Drawing Sheets